United States Patent [19]

Wedemeyer et al.

[11] 4,366,325
[45] Dec. 28, 1982

[54] PROCESS FOR THE PREPARATION OF 3-PHENOXY-BENZALDEHYDES

[75] Inventors: Karlfried Wedemeyer, Cologne; Helmut Fiege, Leverkusen, both of Fed. Rep. of Germany

[73] Assignee: Bayer Aktiengesellschaft, Leverkusen, Fed. Rep. of Germany

[21] Appl. No.: 195,157

[22] Filed: Oct. 8, 1980

[30] Foreign Application Priority Data

Oct. 30, 1979 [DE] Fed. Rep. of Germany ....... 2943805

[51] Int. Cl.³ ............................................. C07C 45/38
[52] U.S. Cl. .................................. 568/432; 252/470; 252/472; 252/444
[58] Field of Search ............................... 568/432, 431

[56] References Cited

U.S. PATENT DOCUMENTS

| | | | |
|---|---|---|---|
| 3,321,526 | 5/1967 | Marchand et al. | 568/432 |
| 4,026,950 | 5/1977 | Le Ludec | 568/432 |
| 4,119,671 | 10/1978 | Bauer et al. | 568/432 |
| 4,190,605 | 2/1980 | Muench et al. | 568/432 |

Primary Examiner—Bernard Helfin
Attorney, Agent, or Firm—Sprung, Horn, Kramer & Woods

[57] ABSTRACT

In a process for the preparation of 3-phenoxy-benzaldehyde by oxidation of 3-phenoxy-benzyl alcohol of the formula

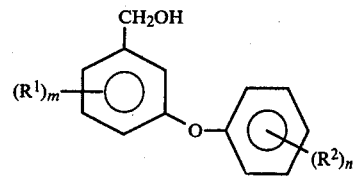

in which
m represents a number from 1 to 4,
n represents a number from 1 to 5 and
$R^1$ and $R^2$ are identical or different and denote hydrogen, halogen, alkyl, cycloalkyl, aralkyl, alkoxy, cycloalkoxy, aryloxy or perfluoroalkyl, with an oxygen containing gas in aqueous alkali at a temperature from the solidification point to the boiling point of the reaction mixture in the presence of a platinum metal catalyst and in the presence of lead and/or bismuth and/or tellurium and/or a compound of said lead, bismuth or tellurium.

11 Claims, No Drawings

PROCESS FOR THE PREPARATION OF 3-PHENOXY-BENZALDEHYDES

BACKGROUND OF THE INVENTION

The invention relates to a process for the preparation of 3-phenoxy-benzaldehydes by catalytic oxidation of 3-phenoxy-benzyl alcohols with oxygen or gases containing oxygen.

DISCUSSION OF PRIOR ART

It is known (Neuere Methoden der präparativen organischen Chemie (Recent Methods of Preparative Organic Chemistry), Volume 2, pages 213 and 214 (1960)), to oxidise benzyl alcohol with oxygen in the presence of $PtO_2$ to give benzaldehyde. However, it is only possible to oxidize benzyl alcohol, an alcohol which is only slightly soluble in water, to benzaldehyde in a solvent in which the alcohol, aldehyde and water of reaction formed are completely soluble. As soon as an aqueous phase appears, the catalyst agglomerizes and the oxidation ceases. n-Heptane is recommended as the best solvent, but benzyl alcohol concentrations of only about 2% can be used in this solvent. The yield of benzaldehyde using this solvent is 78% of theory.

If the oxidation of benzyl alcohol is carried out in an aqueous/alkaline medium in the presence of a platinum-on-charcoal catalyst, no benzaldehyde is formed, but benzoic acid is formed virtually quantitatively.

SUMMARY OF INVENTION

A process has now been found for the preparation of 3-phenoxy-benzaldehydes by oxidation of 3-phenoxy-benzyl alcohols of the formula

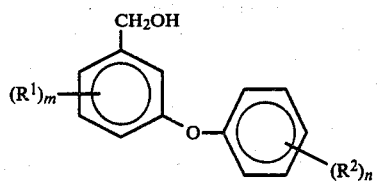

in which
m represents a number from 1 to 4,
n represents a number from 1 to 5 and
$R^1$ and $R^2$ are identical or different and denote hydrogen, halogen, alkyl, cycloalkyl, aralkyl, alkoxy, cycloalkoxy, aryloxy or perfluoroalkyl,
in a liquid phase, which is characterized in that the oxidation is carried out with oxygen or gases containing oxygen, in aqueous alkali, at temperatures from the solidification point to the boiling point of the reaction mixture, in the presence of a platinum metal catalyst and in the presence of lead and/or bismuth and/or tellurium and/or compounds thereof as activators.

Possible alkyl radicals in the formula (I) are straight-chain or branched hydrocarbons with 1 to 12, preferably 1 to 6, carbon atoms.

Alkyl radicals which may be mentioned are: methyl, ethyl, propyl, isopropyl, butyl, isobutyl, sec.-butyl, tert.-butyl, pentyl, isopentyl, tert.-amyl, hexyl, isohexyl, heptyl, isoheptyl, octyl, isooctyl, tert.-octyl, nonyl, isononyl, dodecyl and isododecyl.

Alkyl radicals which may be mentioned as preferred are: methyl, ethyl, propyl, isopropyl, butyl, isobutyl, sec.-butyl, tert.-butyl, pentyl, isopentyl, tert.-amyl and isohexyl.

Possible cycloalkyl radicals are those with 3 to 6, preferably 5 and 6, carbon atoms, such as the cyclopentyl radical and the cyclohexyl radical.

Aryl radicals which may be mentioned are: the phenyl radical and the naphthyl radical, preferably the phenyl radical.

Possible aralkyl radicals are those with 7 to 12, preferably 7 to 9, carbon atoms. Aralkyl radicals which may be mentioned are: the benzyl radical, the α-methyl-benzyl radical, the α,α-dimethyl-benzyl radical and the α-ethylbenzyl radical, preferably the benzyl radical.

Possible alkoxy radicals are those with up to 12, preferably up to 6, carbon atoms. Examples which are mentioned are: methoxy, ethoxy, propoxy, isopropoxy, butoxy, isobutoxy, tert.-butoxy, isopentoxy, hexyloxy, isohexyloxy and methylenedioxy.

Possible cycloalkoxy radicals are those with up to 7, preferably up to 6, carbon atoms. Cycloalkoxy radicals which may be mentioned are preferably the cyclopentoxy radical and the cyclohexyloxy radical.

The phenoxy radical may be mentioned as the preferred aryloxy radical.

Halogens can be fluorine, chlorine, bromine and iodine, preferably fluorine, chlorine and bromine.

Possible perfluoroalkyl radicals are those with up to 4, preferably up to 2, carbon atoms. Examples which are mentioned are: the trifluoromethyl radical and the pentafluoroethyl radical, in particular the trifluoromethyl radical.

3-Phenoxy-benzyl alcohols of the formula

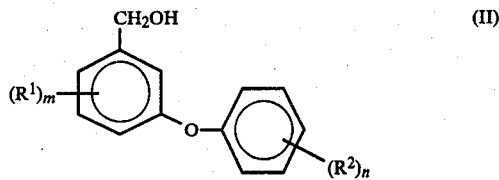

wherein
m represents 1 to 2,
n denotes 1, 2 or 3 and
$R^1$ and $R^2$ are identical or different and represent hydrogen, alkyl with 1 to 6 carbon atoms, alkoxy with 1 to 6 carbon atoms, phenoxy, fluorine, chlorine, bromine or trifluoromethyl,
are preferably employed in the process according to the invention.

3-Phenoxy-benzyl alcohol, 4-fluoro-3-phenoxy-benzyl alcohol, 6-chloro-3-phenoxybenzyl alcohol, 3-(4-methylphenoxy)-benzyl alcohol, 3-(4-chlorophenoxy)-benzyl alcohol, 3-(3,4-dichlorophenoxy)-benzyl alcohol and 3-[3-(trifluoromethyl)-phenoxy]-benzyl alcohol are particularly preferably employed in the process according to the invention.

The preparation of the 3-phenoxy-benzyl alcohols is known. They can be prepared by hydrolysis of 3-phenoxy-benzyl chlorides or 3-phenoxy-benzyl acetates (DE-OS (German Published Specification) No. 2,402,457), by reduction of 3-phenoxy-benzoic acids (U.S. Pat. No. 3,987,140) or esters thereof (Belgian Patent Specification No. 838,193), by reaction of m-hydroxy-benzyl alcohols with halogenobenzenes (Japanese Patent Specification No. 4,861,443), or by oxidation of 3-phenoxy-toluenes (Agric. Biol. Chem. 37, (1973) 2682). Crude mixtures of 3-phenoxy-benzyl alcohols already obtained from such preparation processes can optionally be employed in the oxidation according to the invention.

Possible alkalis are compounds of the alkali metals and/or of the alkaline earth metals, such as the hydroxides, carbonates, bicarbonates, phosphates and borates. The carbonates and/or hydroxides of sodium and/or potassium are particularly preferably employed as the alkali.

The amounts of alkali to be employed in the process according to the invention can vary within wide limits. In general, 0.01 to 3 mols, preferably 0.02 to 1.5 mols, of alkali are employed per 1 mol of the 3-phenoxy-benzyl alcohol to be oxidized.

The alkali can be added to the reaction mixture at the start of the reaction all at once in anhydrous form, or together with water or as an aqueous solution. However, the alkali can also be first added, in anhydrous form or in a solution in water, intermittently or continuously to the reaction mixture in the course of the oxidation.

Since water is formed in the oxidation of 3-phenoxy-benzyl alcohols to give 3-phenoxy-Benzaldehydes, the process necessarily amounts to oxidation in the presence of water. In the process according to the invention it is remarkable that the water does not even interfere with the oxidation when it forms a second liquid phase. It can even be advantageous if the aqueous phase is increased further by adding water.

The volume ratio of aqueous phase to 3-phenoxy-benzyl alcohol to be oxidized (the organic phase) can vary within wide limits. At the start of the reaction, the ratio of aqueous phase to organic phase can be 0:1. This is the case if the oxidation is started using anhydrous alkali and furthermore no water is additionally introduced. The upper limit of the volume ratio of aqueous phase to organic phase is in general not greater than 30:1 for practical reasons. Volume ratios of about 0:1 to about 15:1 have proved particularly suitable.

Other inert organic compounds which are sparingly soluble in water and which function as solvents for the 3-phenoxy-benzyl alcohol and/or the aldehyde formed and become a constituent of the organic phase can also additionally be present in the reaction mixture during the oxidation. Such solvents can be aliphatic and/or aromatic hydrocarbons and/or aliphatic and/or aromatic ethers. Solvents which may be mentioned are: hexane, heptane, iso-octane, benzene, toluene, xylene and 3-phenoxy-toluene.

Platinum metals which are employed in the process according to the invention are platinum, palladium, rhodium, iridium, ruthenium and/or osmium. The platinum metals platinum and/or palladium, especially platinum, are preferably employed.

The platinum metals employed as catalysts can be added to the reaction components in the most diverse forms, for example in elementary, that is to say metallic, form or in the form of compounds, for example as oxides or in the form of other compounds.

The platinum metals can also be applied to supports. Examples of suitable supports are active charcoal, graphite, kieselguhr, silica gel, spinels, aluminium oxide, asbestos, calcium carbonate, magnesium carbonate, barium sulphate or organic supports. Active charcoal, for example the inexpensive pulverulent charcoals produced from wood such as are frequently used for decolorization purposes, is preferably employed as the support.

The platinum metal content of these supported catalysts can vary within wide limits. In general, the platinum metal content is 0.01 to 20% by weight, preferably 0.05 to 10% by weight and particularly preferably 0.1 to 5% by weight.

The amounts in which the platinum metal catalysts are used, relative to the 3-phenoxy-benzyl alcohol, can vary within wide limits. The amounts depend, inter alia, on the desired rate of oxidation. In general, the amounts of the catalysts is less than the amount of 3-phenoxy-benzyl alcohol in the feed mixture. The platinum metal catalysts are usually employed in amounts of 0.1 to 30% by weight, preferably 0.5 to 20% by weight, relative to the 3-phenoxy-benzyl alcohol. The platinum metal catalysts can in general be employed repeatedly for the oxidation.

The activity of the platinum metal catalysts is considerably increased by the presence of lead and/or bismuth and/or tellurium and/or compounds thereof as activators. Not only is this increase in activity remarkable, but it is also remarkable that, in spite of the presence of alkali, the oxidation does not lead to the 3-phenoxy-benzoic acid but leads selectively to the 3-phenoxy-benzaldehyde.

The amounts in which the activators to be used according to the invention are employed can vary within wide limits. The effect of the activator is already clearly noticeable in cases where $5 \times 10^{-6}$ mol of metal or metal compound are added per mol of 3-phenoxy-benzyl alcohol. It is also possible to employ 0.1 mol or more of activator per mol of 3-phenoxy-benzyl alcohol, but these high additions in general provide no particular advantage. The activators are usually added in amounts of $1 \times 10^{-5}$ to $1 \times 10^{-1}$ mol, preferably $2 \times 10^{-5}$ to $2 \times 10^{-2}$ mol, per mol of 3-phenoxy-benzyl alcohol to be oxidised.

The metals to be used, according to the invention, as activators can be employed as such, that is to say in elementary form, and/or in the form of their compounds, for example as oxides, hydroxides, hydrated oxides or oxyacids or as salts of hydracids, such as chlorides, bromides, iodides, sulphides, selenides or tellurides, or as salts of inorganic oxyacids, such as nitrates, nitrites, phosphites, phosphates, carbonates, sulphates, sulphites, perchlorates, antimonates, arseniates, selenides, seleniates, tellurites, tellurates or borates, or as salts of oxyacids which are derived from transition metals, such as vanadates, niobdates, tantalates, chromates, molybdates, tungstates or permanganates, or as salts of organic aliphatic or aromatic acids, such as formates, acetates, propionates, benzoates, salicylates, lactates, mandelates, glyoxylates, arylglyoxylates or citrates, or as phenolates.

The activators can in each case be soluble, partly soluble or insoluble in the reaction mixture.

It is also possible to employ the activators in the process according to the invention in combination with other elements or compounds not claimed as an activator.

The activators according to the invention can be in different and also mixed valency stages, and changes in the valency can also occur during the reaction. If the activators are not already added as oxides and/or hydroxides, it is possible for them to be completely or partly converted into these compounds in the alkaline medium. After the reaction, the platinum metal catalyst can be filtered off with the sparingly soluble activator and used for further oxidation reactions. If appropriate, losses of platinum metal catalysts and/or activators are to be replaced.

The activator can be added to the reaction components as a solid, preferably in finely divided form, or in a dissolved form. It is also possible to already add the activator during the preparation of the platinum metal catalyst or to impregnate the platinum metal catalyst with the activator. The activator can also serve as a support for the platinum metal.

The combination of platinum and lead and/or bismuth and/or tellurium has proved particularly suitable.

The process according to the invention can be carried out at temperatures from the solidification point to the boiling point of the reaction mixture. The solidification point and the boiling point of the reaction mixture depend, inter alia, on the catalyst system, the alkali concentration, the material properties of the feed products and end products and the pressure applied and can easily be determined by preliminary experiments.

The process is preferably carried out at temperatures from 0° to 110° C., particularly preferably at 20° to 100° C.

The platinum metal catalyst, the activator, if it is not already contained in the platinum metal catalyst, the optionally aqueous alkali, the 3-phenoxy-benzyl alcohol and the inert organic solvent optionally also to be used can be brought together in any desired sequence. Thus, it is possible to initially introduce the optionally aqueous alkali into the reaction vessel, to add the catalyst and the activator, and then to add the 3-phenoxy-benzyl alcohol, which is optionally already dissolved in a solvent. However, the reverse sequence can also be followed. It is also possible to add the platinum metal catalyst and the activator to a mixture of the optionally aqueous alkali and the 3-phenoxy-benzyl alcohol (optionally dissolved in a solvent). It is furthermore possible, for example, to initially introduce the platinum metal catalyst, the activator, some of the optionally aqueous alkali and the 3-phenoxy-benzyl alcohol, optionally dissolved in a solvent, into the reaction vessel and to meter in the remainder of the alkali only in the course of the reaction. Only a few of the numerous possibilities are mentioned here. Care should be taken that the components are mixed thoroughly during the reaction.

It is, of course, also possible to oxidize mixtures of different 3-phenoxy-benzyl alcohols.

The process according to the invention can usually be carried out by a procedure in which oxygen or gases containing oxygen, such as air, are brought into contact with a mixture of optionally aqueous alkali, platinum metal catalyst, activator, 3-phenoxy-benzyl alcohol and inert solvent, which is optionally added. In general, the reaction is carried out under atmospheric pressure (1 bar), but the oxidation can also be carried out under higher or lower pressures. In general, the process according to the invention is carried out in the pressure range from 0.5 to 10 bars.

The progress of the oxidation can be followed via the amount of oxygen taken up, and the oxidation is interrupted when the amount of oxygen required for the desired conversion of 3-phenoxy-benzyl alcohol has been taken up. At this stage, the uptake of oxygen usually ceases by itself or slows down. The progress of the reaction can also be established in another manner, for example by determination of the 3-phenoxy-benzaldehyde formed. It may be by all means appropriate to discontinue the reaction when the 3-phenoxy-benzyl alcohol conversion is still incomplete.

For working up, the platinum metal catalyst and the undissolved activator are separated off, for example by filtration. The liquid reaction mixture obtained in general separates into an aqueous-alkaline phase and an organic phase which contains the 3-phenoxy-benzaldehyde. The 3-phenoxy-benzaldehyde can be separated off from the aqueous-alkaline phase, for example, by decanting and/or extraction with an organic solvent which is sparingly soluble in water. An inert solvent which has optionally already been added for the reaction is particularly suitable as the extraction agent. After drying the extraction mixture, the 3-phenoxy-benzaldehyde is obtained by distillation. It is, of course, also possible to isolate the aldehyde in another manner, for example via the corresponding alkali metal bisulphite addition compound.

The 3-phenoxy-benzoic acid formed as a by-product can be liberated from the aqueous-alkaline phase by acidification, and can in general be isolated by filtration. However, it is also possible to use all or some of the still alkaline aqueous phase again in one of the next batches.

3-Phenoxy-benzaldehydes of the formula

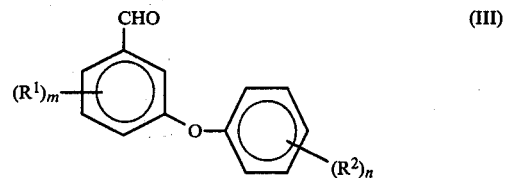

wherein m, n, $R^1$ and $R^2$ have the abovementioned meaning, can be prepared by the process according to the invention.

It is possible to prepare 3-phenoxy-benzaldehydes on an industrial scale by oxidation of 3-phenoxy-benzyl alcohols with oxygen or gases containing oxygen in a simple manner by the process according to the invention. The good yield and high selectivity with which the oxidation reaction proceeds are to be particularly emphasised.

It is completely surprising that, in contrast to the process for the oxidation of benzyl alcohol which is described in the literature, the oxidation according to the invention can be carried out in an aqueous alkaline medium without benzoic acid derivatives being formed in relatively large amounts.

It is furthermore surprising that the activity of the platinum metal catalysts according to the invention was not impaired, although the reaction was carried out in an aqueous medium. It was, in fact, to be expected that the catalyst would be agglomerated by the water of reaction, whereupon the reaction would cease immediately (compare Neuere Methoden der präparativen organischen Chemie (Recent Methods of Preparative Organic Chemistry), Volume 2, page 214, right-hand column (1960)).

The 3-phenoxy-benzaldehydes which can be prepared by the process according to the invention are valuable intermediate products, for example for the synthesis of highly active pyrethroid insecticides and other active compounds with a biological action (see Nachr. Chem. Techn. Lab. 26 (1978), pages 120–122).

The examples which follow are intended to illustrate the process according to the invention, but without restricting it to these examples.

EXAMPLE 1

0.5 g of pulverulent active charcoal with a platinum content of 1% by weight, 100 ml of 0.25 N sodium hydroxide solution, 0.5 ml of 0.5 M $Pb(NO_3)_2$ solution (corresponding to an amount of lead of $2.5 \times 10^{-4}$ mol) and 10.0 g of 3-phenoxy-benzyl alcohol (purity according to gas chromatography: 98.8%) are introduced into a reaction vessel which is provided with a stirrer, thermometer and gas inlet line and can be thermostatically controlled via an external jacket.

After expelling the air from the reaction vessel by oxygen, the stirrer is switched on, the reaction mixture is brought to 80° C. and oxygen is passed into the mixture at this temperature and under normal pressure, whilst stirring vigorously. After 40 minutes, about 0.026 mol of $O_2$ have been taken up and the uptake of oxygen almost ceases.

After filtering off the catalyst, the filtrate (reaction mixture), which consists of an organic phase containing the 3-phenoxy-benzaldehyde and an aqueous-alkaline phase containing the 3-phenoxy-benzoic acid is extracted with ether. After drying the combined ether extracts over sodium sulphate and stripping off the ether under nitrogen, 9.4 g of a residue which, according to analysis by gas chromatography, contains 96.9% of 3-phenoxy-benzaldehyde and 1.3% of still unreacted 3-phenoxy-benzyl alcohol remain. This gives a 3-phenoxy-benzyl alcohol conversion of 98.8%, a 3-phenoxy-benzaldehyde yield of 93% of theory and a selectivity for 3-phenoxy-benzaldehyde of 94%.

0.6 g of 3-phenoxy-benzoic acid of melting point 146° to 147° C., corresponding to 5.7% of theory, relative to the 3-phenoxy-benzyl alcohol employed, is obtained from the aqueous-alkaline phase by acidifying this phase to pH 1 with 20% strength hydrochloric acid and filtering off, washing with a little water and drying the precipitate.

The catalyst which has been filtered off can be reused.

EXAMPLE 2

The procedure followed is as in Example 1, but with the difference that $2.5 \times 10^{-4}$ mol of bismuth in the form of its finely powdered nitrate $Bi(NO_3)_3 \cdot 5H_2O$ is added to the reaction mixture as the activator instead of the lead nitrate. After an oxidation time of 40 minutes, 0.026 mol of $O_2$ has again been taken up and the oxidation virtually ceases. A working up procedure carried out as above gives 9.1 g of 3-phenoxy-benzaldehyde, which, according to gas chromatography, is 97.5% pure and according to oxime titration is 97.8% pure, and 0.7 g of 3-phenoxy-benzoic acid of melting point 146°–147° C. The yield of 3-phenoxy-benzaldehyde is therefore 91% of theory and that of 3-phenoxy-benzoic acid is 7% of theory.

Comparison Example 1

The procedure followed is as in Example 1, but with the difference that neither lead nor bismuth is added to the reaction mixture.

It is established that scarcely any oxygen is taken up without the addition of these activators: after 40 minutes, only 5% of the amount of oxygen otherwise consumed in this period have been taken up. Thereafter, the rate of uptake of $O_2$ decreases still further.

Comparison Example 2

The procedure followed is as in Example 1, but with the difference that only 100 ml of water are added to the reaction mixture instead of the 100 ml of sodium hydroxide solution.

It is established that, in spite of the presence of lead, no oxygen is taken up under these conditions in the absence of alkali (experimental period: over 2 hours).

This experiment, together with Example 1 and Comparison Example 1, shows that the simultaneous presence of alkali and activator is essential to the invention.

EXAMPLE 3 TO 23

These examples were carried out in the apparatus described in Example 1 and in principle by the same procedure. The experimental conditions chosen in an individual case can be found in Table 1. The abbreviation 3-POB is used in Table 1 for the 3-phenoxy-benzyl alcohol employed as the starting compound.

As the results in Table 1 show, the process according to the invention can be carried out with high conversions and with very good 3-phenoxy-benzaldehyde yields and selectivities under very different conditions with regard to temperature, alkali/3-POB ratio, volume ratio of aqueous phase to organic phase, presence of inert organic solvents, weight ratio of catalyst to 3-POB, type of activator, form of activator and activator concentration.

TABLE 1

3-Phenoxybenzyl alcohol (3-POB) under various conditions

| Example No. | 3-POB employed g | 3-POB employed % purity | Mols of NaOH mols of 3-POB | aqueous phase[a] organic phase | g of catalyst[b] g of 3-POB |
|---|---|---|---|---|---|
| 3 | 20 | 49.0[c] | 2.04 | 5:1 | 0.1 |
| 4 | 10 | 98.8 | 1.01 | 10:1 | 0.05 |
| 5 | 10 | 98.8 | 0.06 | 10:1 | 0.05 |
| 6 | 10 | 98.8 | 0.02 | 10:1 | 0.05 |
| 7 | 10 | 98.8 | 0.506 | 10:1 | 0.05 |
| 8 | 10 | 98.8 | 0.506 | 10:1 | 0.05 |
| 9 | 10 | 98.8 | 0.506 | 10:1 | 0.05 |
| 10 | 10 | 97.9 | 0.143 | 10:1 | 0.05 |
| 11 | 10 | 97.9 | 0.143 | 10:1 | 0.05 |
| 12 | 10 | 97.9 | 0.143 | 10:1 | 0.05 |
| 13 | 20 | 97.9 | 0.255 | 5:1 | 0.025 |
| 14 | 40 | 97.9 | 0.128 | 2,5:1 | 0.0125 |
| 15 | 70 | 97.9 | 0.073 | 1,4:1 | 0.0071 |
| 16 | 20 | 97.9 | 0.051 | 0:1 | 0.05 |
| 17 | 10 | 98.8 | 0.506 | 10:1 | 0.05 |
| 18 | 10 | 98.8 | 0.506 | 10:1 | 0.05 |
| 19 | 10 | 98.8 | 0.506 | 10:1 | 0.05 |
| 20 | 10 | 98.8 | 0.506 | 10:1 | 0.05 |
| 21 | 10 | 98.8 | 0.506 | 10:1 | 0.05 |
| 22 | 10 | 98.8 | 0.506 | 10:1 | 0.05 |
| 23 | 20 | 49.0[d] | 0.506 | 5:1 | 0.05 |

| Example No. | Activator added Type | Activator added Mols of activator / Mols of 3-POB | Temperature °C. | Uptake of $O_2$ Mols of $O_2$ / Mols of 3-POB | Uptake of $O_2$ in minutes |
|---|---|---|---|---|---|
| 3 | $Pb(NO_3)_2$ | $5 \times 10^{-3}$ | 30 | 0.47 | 30 |
| 4 | $Bi(NO_3)_3$ | $5 \times 10^{-3}$ | 60 | 0.51 | 35 |
| 5 | $Pb(NO_3)_2$ | $2,5 \times 10^{-3}$ | 98 | 0.51 | 150 |
| 6 | $Pb(NO_3)_2$ | $2,5 \times 10^{-3}$ | 90 | 0.36 | 60 |
| 7 | $Pb(NO_3)_2$ | $2 \times 10^{-2}$ | 80 | 0.53 | 45 |
| 8 | $Pb(NO_3)_2$ | $4 \times 10^{-5}$ | 80 | 0.48 | 45 |

TABLE 1-continued

3-Phenoxybenzyl alcohol (3-POB) under various conditions

| | | | | | |
|---|---|---|---|---|---|
| 9 | Pb(NO$_3$)$_2$ | 2 × 10$^{-5}$ | 80 | 0.36 | 60 |
| 10 | Bi(NO$_3$)$_3$ | 2 × 10$^{-2}$ | 80 | 0.51 | 45 |
| 11 | Bi(NO$_3$)$_3$ | 3 × 10$^{-4}$ | 80 | 0.53 | 45 |
| 12 | Bi(NO$_3$)$_3$ | 4 × 10$^{-5}$ | 80 | 0.50 | 45 |
| 13 | Pb(NO$_3$)$_2$ | 2,5 × 10$^{-3}$ | 80 | 0.52 | 80 |
| 14 | Pb(NO$_3$)$_2$ | 1,3 × 10$^{-3}$ | 80 | 0.50 | 150 |
| 15 | Pb(NO$_3$)$_2$ | 7,3 × 10$^{-4}$ | 80 | 0.51 | 400 |
| 16 | Bi(NO$_3$)$_3$ | 5 × 10$^{-3}$ | 80 | 0.30 | 45 |
| 17 | Pb powder | 5 × 10$^{-3}$ | 80 | 0.52 | 50 |
| 18 | Bi powder | 5 × 10$^{-3}$ | 80 | 0.52 | 45 |
| 19 | Te powder | 5 × 10$^{-3}$ | 80 | 0.5 | 250 |
| 20 | TeO$_2$ | 5 × 10$^{-3}$ | 80 | 0.50 | 200 |
| 21 | H$_6$TeO$_6$ | 5 × 10$^{-3}$ | 80 | 0.50 | 150 |
| 22 | PbO$_2$ | 5 × 10$^{-3}$ | 80 | 0.51 | 55 |
| 23 | Pb(OCOCH$_3$)$_2$ | 5 × 10$^{-3}$ | 80 | 0.55 | 60 |

| Example No. | 3-POB conversion % | 3-Phenoxybenzaldehyde Yield % of theory | Selectivity % | 3-Phenoxybenzoic acid Yield % of theory |
|---|---|---|---|---|
| 3 | 94.0 | 84.6 | 90.0 | 4.3 |
| 4 | 97.6 | 91.6 | 93.9 | 5.6 |
| 5 | 99.0 | 93.4 | 94.4 | 4.7 |
| 6 | 73 | 69.1 | 94.7 | 1.0 |
| 7 | 99 | 90.6 | 91.5 | 7.5 |
| 8 | 93.2 | 89.1 | 95.6 | 3.8 |
| 9 | 69.0 | 66.3 | 96.1 | 2.4 |
| 10 | 97.7 | 90.3 | 92.4 | 5.2 |
| 11 | 99.5 | 91.9 | 92.4 | 6.7 |
| 12 | 95.2 | 88.2 | 93.3 | 5.2 |
| 13 | 98.0 | 91.5 | 93.4 | 5.7 |
| 14 | 96.5 | 90.4 | 93.7 | 4.8 |
| 15 | 99 | 90.1 | 91 | 5.3 |
| 16 | 58.2 | 56.0 | 96.2 | 3.3 |
| 17 | 98.0 | 90.8 | 92.7 | 6.1 |
| 18 | 98.0 | 92.9 | 93.8 | 6.1 |
| 19 | 99 | 93.9 | 94.8 | 3.3 |
| 20 | 95.4 | 90.5 | 94.9 | 4.7 |
| 21 | 95 | 90.2 | 94.9 | 4.7 |
| 22 | 97.4 | 91.3 | 93.7 | 5.2 |
| 23 | ~100 | 86.8 | — | 11.4 |

$^{(a)}$Volume ratio at the start of the oxidation
$^{(b)}$Catalyst = 1% strength platinum-on-active charcoal
$^{(c)}$Remainder: predominantly 3-phenoxytoluene, as the solvent
$^{(d)}$Remainder: predominantly toluene, as the solvent

EXAMPLE 24 TO 29

The oxidation of variously substituted 3-phenoxybenzyl alcohols with oxygen under 1 bar at 80° C. in the presence of 100 ml of 0.25 N sodium hydroxide solution, 0.5 g of pulverulent active charcoal with a platinum content of 1% by weight and 1.25×10$^{-4}$ mol of lead-II nitrate led to the results summarised in Table 2. The apparatus and procedure for the experiments corresponded to those in Example 1.

TABLE 2

Oxidation of substituted 3-phenoxy-benzyl alcohols to give the correspondingly substituted 3-phenoxy-benzaldehydes

| Example No. | Substituted 3-phenoxy-benzyl alcohol employed Name | Amount employed g | Purity % | Uptake of O$_2$ Mols of O$_2$ Mols of 3-POB | in minutes | Alcohol conversion % | Substituted 3-phenoxy-benzaldehyde Yield % of theory | Selectivity % | Substituted 3-phenoxy-benzoic acid Yield % of theory |
|---|---|---|---|---|---|---|---|---|---|
| 24 | 4-Fluoro-3-phenoxy-benzyl alcohol | 10.9 | 96 | 0.51 | 20 | >99 | 95 | — | 4.5 |
| 25 | 6-Chloro-3-phenoxy-benzyl alcohol | 11.7 | 93 | 0.33 | 40 | 56 | 46.2 | 82.5 | 9.5 |
| 26 | 3-(4-Methylphenoxy)-benzyl alcohol | 10.7 | 97 | 0.51 | 30 | 98 | 94.3 | 96.2 | 3.6 |
| 27 | 3-(4-Chlorophenoxy)-benzyl alcohol | 11.7 | 95 | 0.52 | 30 | >99 | 94.5 | — | 4.4 |
| 28 | 3-(3,4-Dichlorophenoxy)-benzyl alcohol | 13.5 | 94 | 0.50 | 30 | 97 | 94.3 | 97.2 | 1.5 |
| 29 | 3-[3-(Trifluoromethyl)-phenoxy]-benzyl alcohol | 13.3 | 95 | 0.50 | 25 | >99 | 97.2 | — | 0.8 |

EXAMPLE 30 TO 32

Oxygen is stirred into mixtures of in each case 10 g of 3-phenoxy-benzyl alcohol, 100 ml of 0.1 N sodium hydroxide solution and 0.5 g of pulverulent medicinal charcoal with a palladium content of 5% by weight, at 80° C. under normal pressure in the apparatus and by the procedure described in Example 1. The mixtures also contain 2.5×10$^{-4}$ mol of bismuth-III nitrate in the case of Example 30 and 2.5×10$^{-4}$ mol of telluric acid (H$_6$TeO$_6$) in the case of Example 31, and no other activator is added in the case of Example 32.

The results summarised in Table 3 show that the oxidation can already be carried out on palladium without the addition of an activator, but that the addition of bismuth or tellurium leads to an improvement in the activity and yield and selectivity:

TABLE 3

Oxidation on palladium

| Example No. | Activator | Time(*) minutes | 3-POB conversion % | 3-Phenoxybenzaldehyde Yield % of theory | Selectivity % | 3-Phenoxybenzoic acid Yield % of theory |
|---|---|---|---|---|---|---|
| 30 | Bi(NO$_3$)$_3$ | 90 | 90 | 75 | 83 | 12 |
| 31 | H$_6$TeO$_6$ | 150 | 98 | 79 | 81 | 15 |
| 32 | none | 250 | 83 | 61 | 73 | 17 |

(*)for the uptake of about 0.5 mol of O$_2$ per mol of 3-POB.

What is claimed is:
1. A process for the preparation of 3-phenoxy-benzaldehyde which comprises contacting 3-phenoxy-benzyl alcohol of the formula

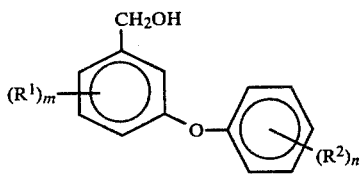

in which m represents a number from 1 to 4 n represents a number from 1 to 5 and $R^1$ and $R^2$ are identical or different and denote hydrogen, halogen, alkyl, cycloalkyl, aralkyl, alkoxy, cycloalkoxy, aryloxy or perfluoroalkyl with an oxygen containing gas in aqueous alkali at a temperature from 0° to 110° C. in the presence of a platinum metal catalyst and in the presence of lead and/or bismuth and/or tellurium and/or a compound of said lead, bismuth or tellurium, said lead and/or bismuth and/or tellurium and/or compound thereof being present in the reaction mixture in an amount of at least $5 \times 10^{-6}$ mol per mol of 3-phenoxy-benzyl alcohol to be oxidized.

2. A process according to claim 1 wherein said platinum metal catalyst is platinum or palladium.

3. A process according to claim 1 wherein palladium is employed as the platinum metal catalyst.

4. A process according to claim 1 wherein platinum is employed as the platinum metal catalyst and said platinum is disposed on a support.

5. A process according to claim 4 wherein said support is activated charcoal.

6. A process according to claim 1 wherein said platinum metal catalyst is present in an amount of 0.01 to 20% by weight, based upon the weight of the metal of the platinum metal catalyst and said catalyst is disposed on a support.

7. A process according to claim 1 wherein 0.01 to 3 mols of alkali are employed per mol of 3-phenoxy-benzyl alcohol to be oxidized.

8. A process according to claim 1 wherein said alkali is a hydroxide and/or carbonate of sodium and/or potassium.

9. A process according to claim 1, wherein the process is carried out in the presence of lead or a compound of lead.

10. A process according to claim 1, wherein the process is carried out in the presence of bismuth or a compound of bismuth.

11. A process according to claim 1, wherein the process is carried out in the presence of tellurium or a compound of tellurium.

* * * * *